United States Patent [19]

Berger et al.

[11] Patent Number: 5,241,065

[45] Date of Patent: Aug. 31, 1993

[54] 2,3,4,5-TETRAHYDRO-1H-3-BENZAZEPINES HAVING ANTI-PSYCHOTIC ACTIVITY

[75] Inventors: Joel G. Berger, Cedar Grove; Wei K. Chang, Livingston; Joseph A. Kozlowski, Plainsboro; Guowei Zhou, West Orange, all of N.J.

[73] Assignee: Schering Corporation, Kenilworth, N.J.

[21] Appl. No.: 841,603

[22] Filed: Feb. 25, 1992

[51] Int. Cl.$^5$ .................... C07D 223/16; A61K 31/55
[52] U.S. Cl. ..................................... 540/523; 540/322; 540/586; 540/594; 514/213
[58] Field of Search ................ 540/522, 523, 586, 594

[56] References Cited

U.S. PATENT DOCUMENTS 5,015,639  5/1991  Berger et al. .................... 540/594

FOREIGN PATENT DOCUMENTS 9104046  12/1991  PCT Int'l Appl. ................ 540/594

OTHER PUBLICATIONS

Ciufolini et al, Tetrahedron Letters 1987, vol. 28 No. 2, 171-174.
Ciufolini et al. J. Org. Chem. [Communications] 1988. 53, 4149-4151.
Piers et al. J. Org. Chem. 1990, 55, 3454-3455.
Negishi et al. J. Am. Chem. Soc., 1989, 111, 8018-8020.
Semmelhack et al. J., Am. Chem. Soc., 1975, 97:9, 2507-2516.
Scott et al. Acc. Chem. Res., 1988, 21, 47-54.

Primary Examiner—Robert T. Bond
Attorney, Agent, or Firm—John H. C. Blasdale; Edward H. Mazer; Steinar V. Kanstad

[57] ABSTRACT

A novel process for the preparation of α-substituted arylacetamides wherein the substituent is an aromatic group or a 1-alkenyl or 1-cycloalkenyl group and wherein the nitrogen atom carries no hydrogen atoms comprises the reaction of an arylacetamide having one or two hydrogen atoms on the α-carbon atom, wherein the nitrogen atom carries no hydrogen atoms, with a strong base in an inert aprotic organic solvent, followed by reaction with a zerovalent transition metal catalyst and then with a compound of the formula $R^4$—X, wherein $R^4$ is selected from aromatic groups, 1-alkenyl groups and 1-cycloalkenyl groups and X is a particular leaving group, especially a triflate group. The α-substituted arylacetamides are useful as intermediates in the preparation (by reduction) of α-substituted arylethylamines, e.g., 1-substituted-2,3,4,5-tetrahydro-1H-3-benzazepines, having pharmacological activity. Certain benzazepines wherein the 1-substituent $R^4$ is 1-(1-cycloalkenyl) are novel.

11 Claims, No Drawings

2,3,4,5-TETRAHYDRO-1H-3-BENZAZEPINES HAVING ANTI-PSYCHOTIC ACTIVITY

BACKGROUND OF THE INVENTION

This invention relates to 2,3,4,5-tetrahydro-1H-3-benzazepines having anti-psychotic activity, and also to the synthesis of α-substituted-arylacetamides, especially fused-ring nitrogen heterocycles, in particular dihydroindoles, 1,2,3,4-tetrahydroisoquinolines and 1,2,3,4,5,6-hexahydro-3-benzazocines, and most particularly 2,3,4,5-tetrahydro-1H-3-benzazepines.

Dihydroindoles, 1,2,3,4-tetrahydroisoquinolines, 1,2,3,4,5,6-hexahydro-3-benzazocines, and particularly 2,3,4,5-tetrahydro-1H-3-benzazepines are known to have useful pharmacological properties. For example, U.S. Pat. Nos. 3,393,192, 3,609,138, 4,011,319, 4,284,555 and 4,477,378, and British Patent Specification no. 1,118,688, all describe 1-phenyl-2,3,4,5-tetrahydro-1H-3-benzazepines having various activities described as antibacterial effects, central nervous system effects and hypotensive effects.

Weinstock et al. in *Drugs of the Future*, Vol. 10, No. 8, pp. 645-697 (1985) discuss the profound effect that 1-phenyl substituents have on the dopaminergic activity of certain types of benzazepines; see in particular Table II on page 666.

European Patent Application No. 83105610.6 (published as 0 096 838) discloses certain 1-aryloxy-2,3,4,5-tetrahydro-1H-3-benzazepines optionally having alkoxy substituents in the 7- and/or 8-position; these compounds are disclosed as having utility in treating depression.

U.S. Pat. No. 5,015,639 describes and claims 2,3,4,5-tetrahydro-1H-3-benzazepines lacking a 1-phenyl group but having instead a variety of 1-substituents including a group of the formula

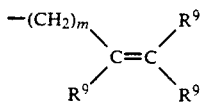

wherein m is 0 or 1, and each of the groups $R^9$, which can be the same or different, is a hydrogen atom or an alkyl, alkoxy, alkoxyalkyl, aralkyl or aryl group. These compounds have good anti-dopaminergic activity, and in particular show surprising selectivity for the D-1 subclassification of dopaminergic receptors. Iorio et al., *Pharmacol. Exp. Ther.* (1983), 226, page 462, and Iorio et al. in *Neurobiology of Central $D_1$-Dopamine Receptors*, pages 1-14 in Advances in Experimental Medicine and Biology 204, Eds. Creese and Breese, Plenum, New York, 1986, have also evaluated the effects of benzazepines on dopamine receptors. Charifson et al., J. Med. Chem. (1988), 31, pages 1941-1946, have similarly evaluated 1,2,3,4-tetrahydroisoquinolines.

International Application No. PCT/US 91/04046 describes and claims (inter alia) compounds having the structural formula A

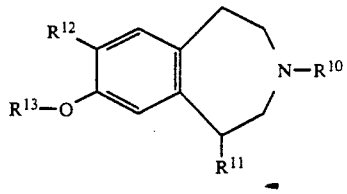

and the pharmaceutically acceptable salts thereof, wherein:

$R^{10}$ represents H, $C_{1-4}$-alkyl, allyl or cyclopropylmethyl;

$R^{11}$ represents $C_{3-8}$-cycloalkyl or $C_{5-8}$-cycloalkenyl;

$R^{12}$ represents $C_{1-4}$-alkyl; and $R^{13}$ represents (inter alia) $R^{12}$, H or $R^{12}CO$.

These compounds are useful in the treatment of psychoses, depression, pain and hypertension.

Ciufolini et al., *Tetrahedron Letters* 1987, Vol. 28 No. 2, 171-174, have described a 'model' intramolecular arylation of 2-[2-(2-iodophenyl)ethyl]-indane-1,3-dione with tetrakis(triphenyphosphine)palladium(0), to yield a spiro(indane-1,3-dione-2,1'-indane), in experiments on the synthesis of Friedricamycin. In further studies of prototype substrates and also of substrates used in studies of the synthesis of Friedricamycin, Ciufolini et al., *J. Org. Chem.* [*Communications*] 1988, 53, 4149-4151, have described intramolecular arylations of 'soft' enolates (i.e., enolates having a $pK_a < 15$) catalyzed by zerovalent palladium. A phenyl halide moiety in one part of the molecule was condensed with an enol in another part of the molecule to provide a benzo-fused five- or sixmembered homocyclic or heterocyclic ring; but compounds with a fused four-membered ring could not be produced. One example in Table I therein shows the formation of an indolone by intramolecular condensation of an N-methyl-N-(2-ethoxycarbonylpropanoyl)-2-iodoanilide. In an adaptation of this method, Piers et al., *J. Org. Chem.* 1990, 55, 3454-3455, have disclosed a five-membered ring annulation method based on Pd(0)-catalyzed intramolecular coupling of a vinyl iodide function with an enolate anion function; in this method, the enolate anion was in a saturated five- or six-membered ring.

A modification of the reaction disclosed by Ciufolini et al. was published by Negishi et al., *J. Am. Chem. Soc.*, 1989, 111, 8018-8020. Using compounds analogous to those which, in the hands of Ciufolini et al., had failed to produce compounds with a fused four-membered ring, there were able to effect a cyclization in the presence of carbon monoxide under pressure: the product was a ketone with its carbonyl group (provided by the carbon monoxide) in a fused five-membered ring. They were similarly able to produce analogous ketones with the carbonyl group in a fused six- or seven-membered ring, and even effect the cyclization on non-cyclic intermediates to produce unfused cyclopentenones.

In all these reactions catalyzed by a zerovalent metal, the enolate is generally stabilized by an adjacent activating group (such as estercarbonyl, keto-carbonyl or nitrite).

SUMMARY OF THE INVENTION

In its broadest aspect the present invention provides a novel process for the preparation of α-substituted arylacetamides wherein the substituent is an aromatic group or a 1-alkenyl or 1-cycloalkenyl group and wherein the nitrogen atom carries no hydrogen atoms;

which comprises the reaction of an arylacetamide having at least one hydrogen atom and preferably two hydrogen atoms on the α-carbon atom, wherein the nitrogen atom carries no hydrogen atoms, with a strong base in an inert aprotic organic solvent;

followed by reaction, in the presence of a zerovalent transition metal catalyst, with a compound of the formula $$R^4-X \qquad (I),$$

wherein $R^4$ is selected from aromatic groups, 1-alkenyl groups and 1-cycloalkenyl groups;

and X is a leaving group, e.g., —OSO₂F or an activated ester group.

The invention further provides novel 1,3,4,5-tetrahydro-2H-3-benzazepines and 2,3,4,5-tetrahydro-1H-3-benzazepines of the formula

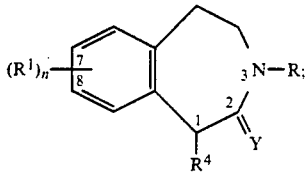

wherein N is 0, 1, 2, 3 or 4;

each $R^1$ is independently selected from alkenyl, alkoxy, hydroxy, alkenyloxy, cycloalkyl, nitro, halogen, phenyl and phenoxy, or two groups $R^1$ in adjacent positions optionally form an alkylenedioxy group or a fused benzene ring, and the phenyl or phenoxy group or the fused benzene ring is optionally substituted by a group selected from alkyl, alkenyl, alkoxy, hydroxy, alkenyloxy, cycloalkyl, nitro, halogen, and alkylenedioxy;

$R^4$ is a 1-cycloalkenyl group;

R is an alkyl, alkenyl, aryl, aralkyl, cycloalkyl or cycloalkylalkyl group;

and Y is an oxygen atom or H₂;

and their non-toxic salts with bases when $R^1$ is or contains a hydroxy group;

and their non-toxic acid addition salts when Y is H₂.

DETAILED DESCRIPTION OF THE INVENTION

It should in particular be noted that the process of the present invention does not require the arylacetamide to have two powerful activating groups (such as ester-carbonyl, keto-carbonyl or nitrile) substituting the α-carbon atom.

The arylacetamide used as starting material can be prepared by standard methods that are well known to those skilled in the art. For example, International Application No. PCT/US 91/04046, the disclosure of which is incorporated herein by reference, describes the preparation of 1,3,4,5-tetrahydro-2H-benzazepin-2-ones of the formula

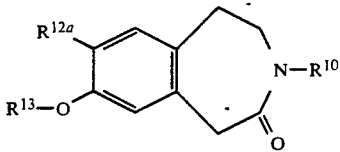

wherein $R^{10}$ and $R^{13}$ are as defined above, and $R^{12a}$ is $R^{12}$ as defined above or a hydrogen or halogen atom. These compounds can be used as starting materials in the process of the present invention.

The arylacetamide is preferably α-unsubstituted and in particular its amide function preferably forms a fused ring with the aryl group, as in a 3-unsubstituted 1,3-dihydro-2H-indol-2-one, 4-unsubstituted 1,2,3,4-tetrahydro-isoquinolin-3-one, 1-unsubstituted 1,3,4,5-tetrahydro-2H-3-benzazepin-2-one or 1-unsubstituted 1,2,3,4,5,6-hexahydro-3-benzazocin-2-one. So the arylacetamide preferably has the formula:

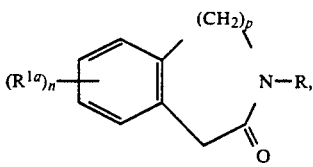

and the 3-substituted 1,3-dihydro-2H-indol-2-one, 4-substituted 1,2,3,4-tetrahydro-isoquinolin-3-one, 1-substituted, 1,3,4,5-tetrahydro-2H-3-benzazepin-2-one or 1-substituted 1,2,3,4,5,6-hexahydro-3-benzazocin-2-one prepared therefrom preferably has the formula

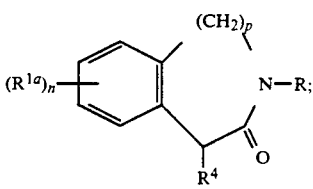

wherein p is 0, 1, 2 or 3 (but preferably 2, as in a 1,3,4,5-tetrahydro2-H-3-benzazepin-2-one);

n is 0, 1, 2, 3 or 4 (but preferably 1 or 2);

each $R^{1a}$ is independently selected from alkyl, alkenyl, alkoxy, alkenyloxy, cycloalkyl, nitro, halogen, phenyl and phenoxy, or two groups $R^{1a}$ in adjacent positions optionally form an alkylenedioxy group or a fused benzene ring, and the phenyl or phenoxy group or the fused benzene ring is optionally substituted by a group selected from alkyl, alkenyl, alkoxy, alkenyloxy, cycloalkyl, nitro, halogen, and alkylenedioxy;

$R^4$ is selected from aromatic groups, 1-alkenyl groups and 1-cycloalkenyl groups;

and R is an alkyl, alkenyl, aryl, aralkyl, cycloalkyl or cycloalkylalkyl group.

It should be noted that compounds of the formula II have an asymmetrically-substituted carbon atom at the 1-position and can exist in optically active forms. All such forms, whether racemic forms or optically active (chiral) forms are covered by the present invention. Similarly, compounds of the formula IV can exist as racemates or optically active forms.

The aryl group of the arylacetamide can be any aryl group, for example a phenyl group or a polycyclic aromatic hydrocarbon group such as 1- or 2-naphthyl, 1-, 2- or 9-anthranyl, 1-, 2-, 3-, 4- or 5-phenanthryl, 4-,5-, 6- or 7-indanyl, 5-, 6-, 7- or 8-[(1,2,3,4-tetrahydro)-naphthyl], or 1-,2-,3- or 4-fluorenyl, or an aromatic heterocyclic group such as 2- or 3-thienyl, 2- or 3-furyl, or such an aromatic heterocyclic group fused to a benzene ring. The aryl group can be substituted, for example by one to three groups selected independently from alkyl, alkenyl, alkoxy, alkenyloxy, nitro, halogen, trifluoromethyl, cyano, cycloalkyl, alkynyloxy, or phenyl or phenoxy, or two adjacent positions can be substituted by alkylenedioxy, and the phenyl or phenoxy group in this list can itself be substituted similarly by alkyl, alkenyl, alkoxy, alkenyoxy, nitro, halogen, trifluoromethyl, cyano, cycloalkyl, alkynyloxy, or alkylenedioxy.

When used herein the following radicals have the assigned meanings:

alkenyl (including the alkenyl portions of alkenyloxy)—represents a straight or branched hydrocarbon chain having at least one carbon-to-carbon double bond and having from 2 to 10, preferably from 2 to 6, carbon atoms; it should especially be noted that, when $R^4$ in the compound of the formula $R^4X$ is an alkenyl group X is attached to said alkenyl group at a carbon atom forming the carbon-carbon double bond;

alkyl (including the alkyl portions of alkoxy, cycloalkylalkyl and aralkyl)—represents a straight or branched, saturated hydrocarbon chain having from 1 to 10 carbon atoms but preferably a lower alkyl group having from 1 to 6 carbon atoms;

alkylene (in particular the alkylene portion of alkylenedioxy)—represents a straight or branched, saturated hydrocarbon chain having from 1 to 6, preferably from 1 to 3, carbon atoms, with the two free valencies on the same carbon atom or on different ones;

aryl (including the aryl portion or aryloxy and aralkyl groups)—represents phenyl, substituted phenyl, 1-naphthyl, 2-naphthyl and indanyl;

cycloalkenyl—represents a carbocyclic group having from 5 to 8, preferably 5 or 6, carbon atoms and one, two or three carbon-to-carbon double bonds in the ring (but preferably only one), and optionally bearing one or two lower alkyl substituents; it should especially be noted that, when $R^4$ in the compound of the formula $R^4X$ is a cycloalkenyl group, the group X is attached to said cycloalkenyl group at a carbon atom bearing a carbon-carbon double bond;

cycloalkyl (including the cycloalkyl portion of cycloalkylalkyl)—represents a saturated carbocylic ring having from 3 to 8, preferably from 5 to 7 carbon atoms;

halogen—represents fluorine, chlorine, bromine and iodine;

aromatic heterocyclic (heteroaryl)—represents a cyclic group having at least one O, S and/or N interrupting a carbocyclic ring structure and having a sufficient number of delocalized pi electrons to provide aromatic character, with the aromatic heterocyclic group having from 2 to 14, preferably from 2 to 8, especially from 2 to 5, carbon atoms, e.g., 2-, 3- or 4-pyridyl, 2- or 3-furyl, 2- or 3-thienyl, 2-, 4- or 5-thiazolyl, 2-,4- or 5-pyrimidinyl, 2-pyrazinyl, 3- or 4-pyridazinyl, 3-, 5- or 6-[1,2,4-triazinyl], 3-or 5-[1,2,4-thiadiazolyl], 2-, 3-, 4-, 5-, 6- or 7-benzofuranyl, 2-, 3-, 4-, 5-, 6- or 7-(1-substituted)-indolyl, 2-, 4- or 5-oxazolyl, etc. Preferred heteroaryl groups are 2-, 3- or 4-pyridyl, 2- or 3-furyl, 2-, 4- or 5-imidazolyl, and 7-(1-substituted)-indolyl (where the 1-substituent is for example methyl);

substituted phenyl—represents a phenyl group in which 1 to 3 hydrogen atoms thereof are replaced by the same or different substituents independently chosen from alkyl, alkenyl, alkoxy, alkenyloxy, nitro, halogen, trifluoromethyl, cyano, cycloalkyl, alkynyloxy, or wherein two hydrogen atoms in adjacent positions are selected from alkylenedioxy.

Certain compounds of the invention, i.e., those for the formula II wherein Y is $H_2$, are basic and form pharmaceutically acceptable salts with organic and inorganic acids. Examples of suitable acids for such salt formation are hydrochloric, sulfuric, phosphoric, acetic, citric, oxalic, malonic, salicyclic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with one equivalent of a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of this invention.

Certain compounds of the invention, i.e., those of the formula II wherein $R^1$ is, or contains, a hydroxy group, are phenolic and therefore acidic in nature. These compounds may form pharmaceutically acceptable salts with strong bases. Examples of such salts are the sodium, potassium and calcium salts. These salts are prepared by contacting the phenol with a sufficient amount of the appropriate base to produce a salt in the conventional manner. The free phenol may be regenerated by treating the salt with one equivalent of a suitable dilute aqueous organic acid solution, e.g., acetic acid or aqueous-alcoholic hydrochloric acid.

The group X of the compound of the formula I ($R^4$—X) is preferably an activated ester group, e.g. a sulfonate ester group such as triflate (trifluoromethane sulfonate), tosylate or mesylate. It can also be a group of the formula—$OSO_2F$. However, the reaction has failed with halogen atoms, even with iodine, as leaving group.

Several appropriate zerovalent transition metal catalysts are commercially available and can be used in the process of the present invention. In these catalysts, the metal itself is preferably palladium, although nickel also works well in this type of reaction. When the transition metal is palladium or nickel, the catalyst will have the formula $M[L]_4$, wherein M is palladium or nickel and L is the ligand. L is preferably a trisubstituted phosphine, in particular a triarylphosphine wherein the aryl group is phenyl or even a heteroaryl group such as furanyl-2. Although L in the compound of the formula $M[L]_4$ can be a trialkylphosphine such as trimethylphosphine or triethylphosphine, the relative instability of these trialkylphosphine compounds—they tend to be pyrophoric—makes them less desirable.

Preferred palladium-containing or nickel-containing catalysts include tetrakis(triphenylphosphine)-palladium(0), tetrakis(triphenylphosphine)-nickel(0), tetrakis[tri(furanyl-2)phosphine]-palladium(0), tetrakis[tri(furanyl-2)]phosphine)-nickel(0), and tris(dibenzylideneacetonyl)bis-palladium(0) ($Pd_2(DBA)_3$). Of these, tetrakis(triphenylphosphine)-palladium(0) is especially preferred for reasons of cost, commercial availability, convenience of use, and efficacy. Alternatively, it can be prepared by reaction of PdCl$_2$ with triphenylphosphine under reduction, e.g., with n-butyllithium. Palladium catalysts of this type that are not commercially available can be prepared by known methods; for example, from Pd$_2$(DBA)$_3$ and the phosphine.

The compound of the formula I is preferably used in a small excess over the compound of the formula III, e.g., 1.05 to 1.1 moles, preferably about 1.06 moles, of I per mole of III. The catalyst is used preferably in an amount of 0.05 to 0.1 moles per mole of reactant of the formula I.

The radical X in the compound R$^4$—X (of the formula I) can be an activated ester such as triflate (trifluoromethane sulfonate), tosylate or mesylate. It can also be a group of the formula—OSO$_2$F. It should in particular be noted that the process according to the invention could not be carried out on a compound of Formula I wherein X is a halogen atom, even iodine; see the comparative Example, Part B of Example 1 below. This failure clearly distinguishes the present invention from the process described by Ciufolini et al., *J. Org. Chem.* [*Communications*] 1988, 53, 4149–4151, wherein the intramolecular arylation of 'soft' enolates catalyzed by zerovalent palladium is effected by means of an aryl halide.

The process according to the invention is carried out under an inert atmosphere, e.g., argon or nitrogen, and at a convenient temperature and for a convenient time, e.g., ambient up to about 60° C. for 2 to 100 hours, preferably 4 to 50 hours, more preferably 6 to 12 or even 24 hours. The reaction requires an inert aprotic organic solvent such as an ether, e.g. THF or DME, or a hydrocarbon, e.g. an aromatic hydrocarbon such as benzene, or mixtures thereof.

Examples of the strong base include lithium diisopropylamide (LDA) and lithium hexamethyldisilazane (LiHMDS) and the like.

The immediate products of the process according to the invention, namely the α-substituted arylacetamides, may have one or more chirally substituted carbon atoms and therefore may exist in isomeric forms. In particular, compounds of the formula IV (such as (R,S)-1-R$^4$-1,3,4,5-tetrahydro-2H-3-benzazepin-2-ones), have an asymmetric center at C-1 and can be resolved, e.g., into their (R)- and (S)-forms. However, this resolution can if desired be carried out at a later stage in the preparation of compounds having pharmacological utility.

These immediate products of the reaction, namely the α-substituted arylacetamides, e.g., the compounds of the formula IV (such as (R,S)-1-R$^4$-1,3,4,5-tetrahydro-2H-3-benzazepin-2-ones) can be used as intermediates in the preparation (by reduction) of α-substituted arylethylamines having pharmacological utility. For example, a 1-R$^4$- 1,3,4,5-tetrahydro-2H-3-benzazepin-2-one can be reduced, preferably with a hydride reducing agent (e.g., in an anhydrous ether solvent with lithium aluminum hydride or with aluminum hydride) to a corresponding 1-substituted-2,3,4,5-tetrahydro-1H-3-benzazepine; further optional steps may also have to be carried out to provide a compound having pharmacological utility, such as the removal of a protecting methyl group from a methoxy substituent (for example, by means of an alkali metal alkylsulfide in an organic aprotic solvent such as DMF, DMSO or DMA, especially sodium ethylsulfide in DMF. The (R)- and (S)-isomers can (if necessary) be separated by known methods at an appropriate point in the synthesis and preferably before the reduction, e.g., by chromatography on a Chiracel OD column with ethanol:hexane (5:95). The product will be a 1-substituted-2,3,4,5-tetrahydro-1H-3-benzazepine having potential pharmacological utility. Compounds in this last-named class include (R)-7-chloro-8-hydroxy-3-methyl-1-phenyl 2,3,4,5-tetrahydro-1H-3-benzazepine (SCH 23390). Other products of the formula IV can if desired be put through these same finishing steps.

Thus the following compounds can be prepared by the novel process of the present invention:

1,3,4,5-Tetrahydro-2H-3-benzazepin-2-ones:
(R,S)-7-chloro-1-(1-cyclohexenyl)-8-methoxy-3-methyl-1,3,4,5-tetrahydro-2H-3-benzazepin-2-one and its (R)- and (S)- isomers;
(R,S)-1-(1-cyclohexenyl)-8-methoxy-3,7-dimethyl-1,3,4,5-tetrahydro-2H-3-benzazepin-2-one and its (R)- and (S)- isomers;
(R,S)-7-chloro-1-(1-cyclopentenyl)-8-methoxy-3-methyl-1,3,4,5-tetrahydro-2H-3-benzazepin-2-one and its (R)- and (S)- isomers;
(R,S)-7-chloro-8-methoxy-3-methyl-1-(2-methyl-1-cyclopentenyl)-1,3,4,5-tetrahydro-2H-3-benzazepin-2-one and its (R)- and (S)- isomers;
(R,S)-7-chloro-8-methoxy-3-methyl-1-(2-methyl-1-cyclohexenyl)-1,3,4,5-tetrahydro-2H-3-benzazepin-2-one and its (R)- and (S)- isomers; and
(R,S)-7-chloro-8-methoxy-3-methyl-1-(1,2-dimethyl-1-propenyl)-1,3,4,5-tetrahydro-2H-3-benzazepin-2-one and its (R)- and (S)- isomers.

2,3,4,5-Tetrahydro-1H-3-benzazepines (by reduction and O-demethylation of the compounds listed above):
(R,S)-7-chloro-1-(1-cyclohexenyl)-8-hydroxy-3-methyl-2,3,4,5-tetrahydro-1H-3-benzazepine, m.p. of hydrobromide 177°–179° C.;
(R,S)-1-(1-cyclohexenyl)-8-hydroxy-3,7-dimethyl-2,3,4,5-tetrahydro-1H-3-benzazepine (as hydrochloride);
(R,S)-7-chloro-1-(1-cyclopentenyl)-8-hydroxy-3-methyl-2,3,4,5-tetrahydro-1H-3-benzazepine, m.p. of free base 186°–188° C.;
(R,S)-7-chloro-8-hydroxy-3-methyl-(2-methyl-1-cyclopentenyl)-2,3,4,5-tetrahydro-1H-3-benzazepine (as hydrochloride); and
(R,S)-7-chloro-8-hydroxy-3-methyl-(2-methyl-1-cyclohexenyl)-2,3,4,5-tetrahydro-1H-3-benzazepine (as hydrochloride).

Resolved enantiomers of 2,3,4,5-tetrahydro-1H-3-benzazepines:
(R)-1-(1-cyclohexenyl)-8-hydroxy-3,7-dimethyl-2,3,4,5-tetrahydro-1H-3-benzazepine (as hydrochloride):
(S)-1-(1-cyclohexenyl)-8-hydroxy-3,7-dimethyl-2,3,4,5-tetrahydro-1H-3-benzazepine (as hydrochloride);
(R)-7-chloro-1-(1-cyclohexenyl)-8-hydroxy-3-methyl-2,3,4,5-tetrahydro-1H-3-benzazepine (as hydrochloride);
(S)-7-chloro-1-(1-cyclohexenyl)-8-hydroxy-3-methyl-2,3,4,5-tetrahydro-1H-3-benzazepine (as hydrochloride);
(S)-7-chloro-8-hydroxy-3-methyl-1-(1,2-dimethyl-1-propenyl)-2,3,4,5-tetrahydro-1H-3-benzazepine (as hydrochloride);
(S)-7-chloro-8-hydroxy-3-methyl-1-(2-methyl-1-cyclopentenyl)-2,3,4,5-tetrahydro-1H-3-benzazepine, m.p. of hydrochloride 248°–249° C. (dec.); and especially (R)-7-chloro-8-hydroxy-3-methyl-1-(2-methyl-1-cyclopentenyl)-2,3,4,5-tetrahydro-1H-3-benzazepine, m.p. of hydrochloride 249°–251° C. (dec.).

Compounds of the formula

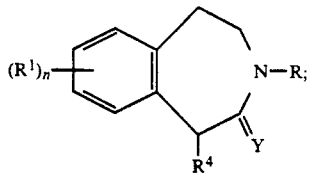

(II)

defined above, and their salts, are novel. Preferred compounds of the formula II include compounds wherein:
n is 1 or 2;
each $R^1$ is independently selected from lower alkoxy, hydroxy, halogen, nitro and phenoxy;
$R^4$ is a 1-cycloalkenyl group;
R is a lower alkyl group;
and Y is $H_2$.

These compounds have valuable pharmacological properties, for example they have anti-psychotic activity, and in particular selectively antagonize the dopamine D-1 receptors. Particularly preferred compounds of the formula II include those of the formula

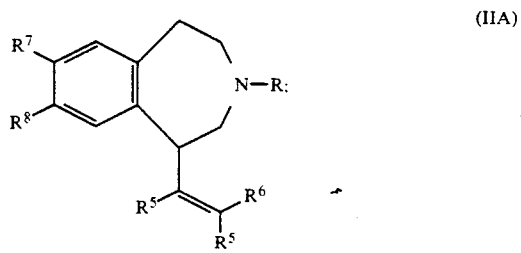

(IIA)

wherein R is as defined above but is preferably a methyl group;
the two groups $R^5$ together form a pentamethylene or especially a trimethylene or a tetramethylene group;
$R^6$ is a lower alkyl group, preferably a methyl group, or a hydrogen atom;
and each of $R^7$ and $R^8$ is independently selected from lower alkoxy, hydroxy and halogen.

Preferably, $R^7$ is halogen and $R^8$ is hydroxy. Most preferably, $R^7$ is chlorine.

In particular, the (R)- isomers of the compounds of formula II wherein Y is $H_2$ and formula IIA are generally preferred to the racemates, and the racemates are generally preferred to the (S)-isomers.

The utility of the compounds of Formula II wherein Y is $H_2$ may be demonstrated by test procedures designed to indicate their antipsychotic activity.

CONDITIONED AVOIDANCE SUPPRESSION (CAR) IN PARTS

Clinically active antipsychotic drugs are known to depress discrete trial avoidance behavior at doses that do not retard the escape response [*Ann. N.Y. Acad. Sci.* 66, 740 (1957)]. A series of experiments was carried out to assess the ability of the compounds of this invention to suppress the conditioned avoidance response (CAR) in rats.

Materials and Methods

Rats were required to jump onto a platform located 6.75 inches (17.15 cm) above the grid floor of an experimental chamber in response to a 5-second tone to avoid a 10-second foot shock (0.6 ma). Each experimental session consisted of 20 such trials presented at 30-second intervals. A correct CAR is scored whenever the rat jumps onto the platform during the tone (prior to foot shock). An escape response is scored when the rat jumps onto the platform during a shock. A response failure is defined as the lack of an escape response during the 10-second shock period.

Groups of 6-8 rats were trained in two consecutive days (total of 40 trials). Rats that reached criterion on day 2 (correct CARs in 16 or more of the 20 trials) were treated with either a test drug or a vehicle on day 3. Suppression of CAR was analyzed statistically using Student's t-test comparing the performances of drug-treated to vehicle-treated rats. The minimal effective dose (MED) for each drug is defined as the lowest dose tested that significantly ($P < 0.05$) reduced avoidance responses.

When tested by the above procedure, representative compounds of the invention and reference compounds showed a dose-related specific blockade of conditioned avoidance response as set form in Table 1 below:

TABLE 1

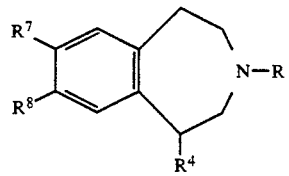

| Compound | $R^4$ | R | $R^7$ | $R^8$ | Rat CAR, mg/kg |
|---|---|---|---|---|---|
| A; (±)-(R, S) (Reference) | 1-(1-cyclohexenyl) | $CH_3$ | $CH_3$ | OH | >30, po (per oral) |
| B; (+)-(S) (Reference) | 1-(1-cyclohexenyl) | $CH_3$ | $CH_3$ | OH | >30, po |
| C; (−)-(R) (Reference) | 1-(1-cyclohexenyl) | $CH_3$ | $CH_3$ | OH | 0.1, sc (subcutaneous) |
| D; (±)-(R, S) (Reference) | 1-(1-cyclopentyl) | $CH_3$ | Cl | OH | >30, po; 3, sc |
| E; (±)-(R, S) (Reference) | 1-cyclohexyl | $CH_3$ | $CH_3$ | OH | 10, po; 3, sc |
| G; (±)-(R, S) | 1-(2-methyl-1- | $CH_3$ | Cl | OH | 10, po; 50, po, |

TABLE 1-continued

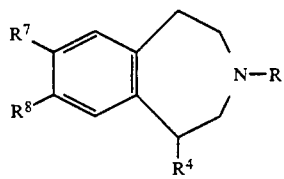

| Compound | R⁴ | R | R⁷ | R⁸ | Rat CAR, mg/kg |
|---|---|---|---|---|---|
| | cyclopentenyl) | | | | at 6 hours; 0.01, sc |
| H; (−)-(R) | 1-(2-methyl-1-cyclopentenyl) | CH₃ | Cl | OH | 5, po; 25, po, at 6 hours |
| J; (+)-(S) | 1-(2-methyl-1-cyclopentenyl) | CH₃ | Cl | OH | >30, po |
| L; (+)-(S) | 1-(1-cyclohexenyl) | CH₃ | Cl | OH | >30, po |
| M; (−)-(R) | 1-(1-cyclohexenyl) | CH₃ | Cl | OH | 10, po |
| N; (±)-(R, S) | 1-(2-methyl-1-cyclohexenyl) | CH₃ | Cl | OH | 30, po |
| P; (±)-(R, S) | 1-(1,2-dimethyl-1-propenyl) | CH₃ | Cl | OH | 10, po |

SUPPRESSION OF CONDITIONED AVOIDANCE RESPONSE (CAR) IN SQUIRREL MONKEYS

This test is designed to measure the effective duration of candidate compounds.

Male or female squirrel monkeys weighing 800–1200 g housed one per cage are utilized. Initially each monkey is taught to terminate both a 3mA electric shock delivered through the grid floor of the test cage and an overlapping tone by depressing a lever in the cage. The monkeys do not proceed to the second phase of testing unless they depress the lever during the shock component of the trials at least 75% of the time during 60 daily trials on three consecutive days.

In the second phase of the testing, a ten second tone is turned on prior to the shock component. A lever pass during the sounding of the tone terminates the tone and prevents the occurrence of the shock component and is denoted as an "avoidance". Compound testing does not begin until the monkey makes at least 85% correct avoidances for five consecutive days.

The compound testing is commenced after three consecutive days of re-testing. The monkey first is injected or orally dosed with the vehicle only and re-tested to show that the vehicle does not affect the response of the monkey. The monkey must achieve at lest an 85% correct avoidance before drug testing commences. If this minimal avoidance level is achieved, the next day the monkey is orally dosed or injected with the subject compounds in the appropriate vehicle, and the number of avoidances are recorded. An animal is defined as having been "affected" by any drug treatment if there is a 50% loss of avoidance behavior relative to the performance of the animal when only the vehicle is injected. The minimal effective dose (MED) is defined as that dose producing an effect in at least 50% of the animals.

A test may be conducted to determine the effective duration of a compound in accordance with the present invention by comparing a compound of the invention to the known compound SCH 23390. A compound of the invention administered 60 minutes prior to the test is compared to SCH 23390 administered 30 minutes prior to test. The duration of each compound is determined by administering a 12.0 mg/kg p.o. dose six hours prior to testing. The ability to decrease significantly the number of avoidances six hours after injection indicates that the compound is still active at that time. Results for representative compounds of the invention and for reference compounds are shown in Table 2 below.

TABLE 2

| Compound | R⁴ | R | R⁷ | R⁸ | Monkey CAR, mg/kg |
|---|---|---|---|---|---|
| A; (±)-(R,S) (Reference) | 1-(1-cyclohexenyl) | CH₃ | CH₃ | OH | 3, po; 10, po, at 1 hour |
| G; (±)-(R,S) | 1-(2-methyl-1-cyclopentenyl) | CH₃ | Cl | OH | 5, po; 20, po, at 6 hours |
| H; (−)-(R) | 1-(2-methyl-1-cyclopentenyl) | CH₃ | Cl | OH | 2, po; 10, po, at 4 hours |

COMPETITIVE INHIBITION ASSAY

Many compounds capable of effecting reproducible physiological changes in neural tissues are believed to operate by binding at one or more receptor sites. Compounds which interact strongly with these receptor sites in in vitro tests, using homogenates of the target organ or structure, are expected to exhibit similar properties when administered in vivo and therefore are candidates for continued study as potential therapeutic and/or diagnostic agents.

Binding of a compound to a receptor site, in vitro, is demonstrated by the specifically of binding and the saturability of the available sites. A methodology for characterization of binding and an interpretation of the data are described by Billard et al., *Life Sciences* 35, 1885 (1984) in which the binding of (R)-(+)-7-chloro-8-hydroxy-3-methyl-1-phenyl-2,3,4,5-tetrahydro-1H-3-benzazepine (SCH 23390) (as its hemi-maleate) to the dopamine D-1 receptor is characterized.

Materials and Methods

Tritiated SCH 23390 and tritiated spiperone (a potent D-2 ligand) were obtained as described in the Billard et al. reference supra and serially diluted in 0.05 M Tris buffer, pH 7.4, as required. A compound of the invention was diluted in 0.05 M Tris buffer, pH 7.4, as required.

Tissue Preparation

Male Sprague-Dawley rats (200 to 250 g) from Charles River Breeding Laboratories, Mass., were used to obtain brain tissue. The rats were humanely sacrificed and their brains removed and placed on ice. Striatal tissue was excised, pooled, and homogenized (Brinkman Polytron, 10 sec) in 100 volumes (w/v) of ice cold 50 mM Tris buffer, pH 7.4 (at 25° C.). The homogenate was centrifuged at 20,000 x g for 10 min. The resulting pellet was re-homogenized in Tris buffer and centrifuged again. The final pellet was resuspended in 50 mM Tris buffer, pH 7.4 containing 120 mM NaCl, 5 mM KCl, 2 mM $CaCl_2$, and 1 mM $MgCl_2$.

Assay

Polypropylene incubation tubes received 100 μl of the individual test compounds at various concentrations dissolved or suspended in 0.05 M Tris buffer, pH 7.4 containing 4 mg/ml methylcellulose, 100 μl of a solution of $^3H$-SCH 23390 in Tris buffer (final reaction mixture concentration=0.3nM) or 100 μl of a solution of $^3H$-spiperone in Tris buffer (final concentration=0.2 nM) and 800 μl of tissue suspension (ca. 3 mg/assay). Tubes were incubated at 37° C. for 15 minutes and rapidly vacuum filtered through Whatman GF/B filters and rinsed 4 times with 4 ml of ice cold 50 mM Tris buffer, pH 7.4. The filters were transferred to scintillation vials, equilibrated with 10 ml of scintillant (Scintosol, Isolab, Inc.) for 16 hours at 25° C., and the radioactivity was determined in a liquid scintillation counter. $K_i$ values were determined as described by Billard et al. using the relationship: $K_i = IC_{50}/(1+([L]K_D))$ wherein $IC_{50}$=concentration of test drug necessary to displace 50% of specifically bound $^3H$-SCH 23390, [L]=concentration of radioligand used in the assay, and $K_D$=dissociation constant.

The inhibition constants ($K_i$) determined from this assay for compounds of the invention and for reference compounds are as shown in Table 3 below:

TABLE 3

| Compound | $R^4$ | R | $R^7$ | $R^8$ | $K_i$ (nM) against $^3H$—SCH 23390 | $^3H$-spiperone |
|---|---|---|---|---|---|---|
| A; (±)-(R,S) (Reference) | 1-(1-cyclohexenyl) | $CH_3$ | $CH_3$ | OH | 8.7 | 1876 |
| B; (+)-(S) (Reference) | 1-(1-cyclohexenyl) | $CH_3$ | $CH_3$ | OH | 101 | 4370 |
| C; (−)-(R) (Reference) | 1-(1-cyclohexenyl) | $CH_3$ | $CH_3$ | OH | 4 | 1670 |
| D; (±)-(R,S) (Reference) | 1-(1-cyclopentyl) | $CH_3$ | Cl | OH | 21 | 1538 |
| E; (±)-(R,S) (Reference) | 1-cyclohexyl | $CH_3$ | $CH_3$ | OH | 48 | 3606 |
| F; (−)-(R) (Reference) | 1-cyclopentyl | $CH_3$ | $CH_3$ | OH | 44 | 1055 |
| G; (±)-(R,S) | 1-(2-methyl-1-cyclopentenyl) | $CH_3$ | Cl | OH | 0.27 | 656 |
| H; (−)-(R) | 1-(2-methyl-1-cyclopentenyl) | $CH_3$ | Cl | OH | 0.43 | 358 |
| J; (+)-(S) | 1-(2-methyl-1-cyclopentenyl) | $CH_3$ | Cl | OH | 15 | 3694 |
| K; (±)-(R,S) | 1-(1-cyclohexenyl) | $CH_3$ | Cl | OH | 2.2 | 1442 |
| L; (+)-(S) | 1-(1-cyclohexenyl) | $CH_3$ | Cl | OH | 23 | 2076 |
| M; (−)-(R) | 1-(1-cyclohexenyl) | $CH_3$ | Cl | OH | 0.87 | 1087 |
| N; (±)-(R,S) | 1-(2-methyl-1-cyclohexenyl) | $CH_3$ | Cl | OH | 0.83 | 420 |
| P; (±)-(R,S) | 1-(1,2-dimethyl-1-propenyl) | $CH_3$ | Cl | OH | 2.8 | 554 |
| Q; (±)-(R,S) | 1-(1-cyclopentenyl) | $CH_3$ | Cl | OH | 2.3 | 595 |

The comparatively small $K_i$ values of the compounds of the invention in the competitive binding assay with SCH 23390 indicate that the compounds of formula II wherein Y is $H_2$ bind strongly to the D-1 receptor site. The relatively high $K_i$ values for the D-2 site, for which spiperone is highly selective, indicate that the compounds are not specifically bound to that receptor site.

The compounds of this invention are substantially non-toxic at the therapeutic close, as is shown in the following Table 4, which compares them with related reference compounds:

TABLE 4

| Compound | $R^4$ | TOXICITY R | $R^7$ | $R^8$ | Toxicity, rat |
|---|---|---|---|---|---|
| A; (±)-(R,S) (Reference) | 1-(1-cyclohexenyl) | $CH_3$ | $CH_3$ | OH | 10 mpk po caused salivation in 1 of 3 rats after 1 hour and in 3 of 3 rats after 6 hours |
| E; (±) (Reference) | 1-cyclohexenyl | $CH_3$ | $CH_3$ | OH | Lethal at 300 mpk |
| F; (−)-(R) (Reference) | 1-cyclopentyl | $CH_3$ | $CH_3$ | OH | Lethal at 300 mpk |
| G; (±)-(R,S) | 1-(2-methyl-1-cyclopentenyl) | $CH_3$ | Cl | OH | Non-toxic at 300 mpk in the rat |
| H; (−)-(R) | 1-(2-methyl-1-cyclopentenyl) | $CH_3$ | Cl | OH | Non-toxic at 150 mpk in the rat |
| M; (−)-(R) | 1-cyclohexenyl | $CH_3$ | Cl | OH | Secretions at 300 mpk |

TABLE 4-continued

| | | TOXICITY | | | |
|---|---|---|---|---|---|
| Compound | $R^4$ | R | $R^7$ | $R^8$ | Toxicity. rat |
| | | | | | in the rat |

The active compounds can be administered orally, transdermally, rectally, or parenterally, for example in the treatment of psychoses. The preferred mode of administration is orally or intravenously.

The compounds of the formula II wherein Y is $H_2$ or IIA can be administered in conventional oral dosage forms such as capsules, tablets, pills, powders, suspensions or solutions prepared with conventional pharmaceutically acceptable excipients and additives, using conventional techniques. Parenteral preparations, i.e., sterile solutions or suspensions, are also made by conventional means.

Pharmaceutical compositions containing the compounds described by this invention can include solid or liquid inert, pharmaceutically acceptable carriers. Solid form preparations include powders, tablets, dispersible granules, capsules, cachets and suppositories. The powders and tablets may comprise from about 5 to 70 percent active ingredient. Suitable solid carriers are known in the art, e.g., magnesium carbonate, magnesium stearate, talc, sugar, and/or lactose. Tablets, powders, cachets and capsules can be used as solid dosage forms suitable for oral administration.

Liquid form preparations include solutions, suspensions and emulsions. As an example may be mentioned water or water-propylene glycol solutions for parenteral injection.

Also included are solid form preparations which are intended for conversion, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that, after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion liquid doses are so prepared, it is preferred to maintain the unused portion of said liquid doses at low temperature (i.e., under refrigeration) in order to retard possible decomposition. The solid form preparations intended for conversion to liquid form may contain flavoring agents, coloring agents, stabilizers, buffers, artificial and natural sweeteners, dispersing agents, thickeners, solubilizing agents and the like, in addition to the active material. The solvent utilized for preparing the liquid form preparation may be water, isotonic water, ethanol, glycerine, propylene glycol and the like as well as mixtures thereof. Naturally, the solvent utilized will be chosen with regard to the route of administration; for example, liquid preparations containing large amounts of ethanol are not suitable for parenteral use.

The compounds of the invention may also be delivered transdermally. The transdermal compositions can take the form of creams, lotions, aerosols and/or emulsions and can be included in a transdermal patch of the matrix or reservoir type as is conventional in the art for this purpose.

For preparing suppositories, a low-melting wax such as mixture of fatty acid glycerides or cocoa butter is first melted, and the active ingredient is dispersed homogeneously therein as by stirring. The molten homogeneous mixture is then poured into conveniently sized molds, allowed to cool and thereby solidify.

Preferably, the pharmaceutical preparation is in unit dosage form, each unit dose containing an appropriate quantity of the active ingredient, e.g., an effective amount to achieve the desired purpose. The novel compounds are preferably administered at about 0.2 to 10 mg/kg. of body weight. Dosage units preferably contain from 5 to 250 mg, preferably 20 to 100 mg, of active ingredient. A typical daily dosage will be from 10 to 500 mg, preferably form 20 to 250 mg.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions (e.g., two, three or four) during the day if desired.

The following Examples illustrate but do not in any way limit the present invention:

EXAMPLE 1

Part A: Preparation of (R,S)-7-Chloro-1-(1-cyclohexenyl)-8-methoxy-3-methyl-1,3,4,5-tetrahydro-2H-3-benzazepin-2-one

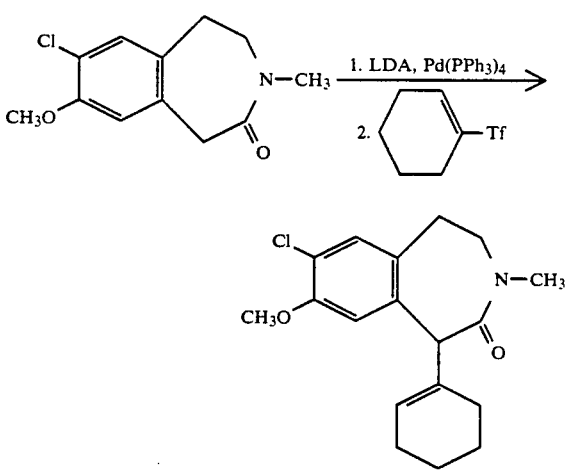

Tf = triflate (trifluoromethanesulfonate)

A mixture of 0.48 g. (2 mmol.) of 7-chloro-8-methoxy-3-methyl-1,3,4,5-tetrahydro-2H-3-benzazepin-2-one, 0.2.g. (0.17 mmol.) of tetrakis(triphenylphosphine)palladium and 10 ml. of THF was cooled in a dry ice/ 2-propanol bath to about −78° C. Under a nitrogen atmosphere, 1.3 ml. of 1.5 M lithium diisopropylamide (2 mmol.) in a cyclohexane was added through a syringe. The mixture was kept at −78° C. for an hour. A solution of 0.50 g (2.2 mmol.) of 1-cyclohexenyl triflate in 10 ml. of THF was then added. The mixture was allowed to warm to room temperature and stirred for an hour, and then heated for 24 hours at 45° C.

10 ml. of water was added to quench the reaction, and the crude product was extracted with ethyl acetate. Liquid chromatography (flash chromatography using hexane:ethyl acetate 1:1 to 1:4) gave pure (R,S)-7-chloro-1-(1-cyclohexenyl)-8-methoxy-3-methyl-1,3,4,5-tetrahydro-2H-3-benzazepin-2-one, which was recrystallized from ethyl acetate to provide a white solid (yield 70%), m.p. 126°–127° C.; thin layer chromatography (TLC): $R_f$0.63 (ethyl acetate); $^1$H NMR (300 MHz, CDCl$_3$): δ 1.5–1.8 (4H, m), 1.9–2.2 (4H, m), 2.85–3.15 (3H, m), 3.05 (3H, s), 3.89 (3H, s), 4.4 (2H, m), 5.0 (1H, bs), 6.6 (1H, s), 7.15 (1H, s); MS FAB-NBA-DMSO, m/e (%): 322 (39), 320 (MH$^+$, 100), 292 (7), 290 (9), 239 (11), 212 (6), 210 (15).

The product of Example 1 Part A can be resolved, e.g. by chromatography on a Chiracel column, and then one or both isomers can be reduced. Thus the (R)-isomer will yield (R)-7-chloro-1-(1-cyclohexenyl)-8-methoxy-3-methyl-2,3,4,5-tetrahydro-1H-3-benzazepine, which in turn can be demethylated to yield (R)-7-chloro-1-(1-cyclohexenyl)-8-hydroxy-3-methyl-2,3,4,5-tetrahydro-1H-3-benzazepine; a compound having pharmacological properties. Alternatively, the resolution can be effected at a later stage in the synthesis.

Part B: COMPARATIVE EXAMPLE according to the process described by Ciufolini et al., *J. Org. Chem.* [*Communications*] 1988, 53, 4149–4151.

Attempted Preparation of (R,S)-7-Chloro-1-(1-cyclohexenyl)-8-methoxy-3-methyl-1,3,4,5-tetrahydro-2H-3-benzazepin-2-one

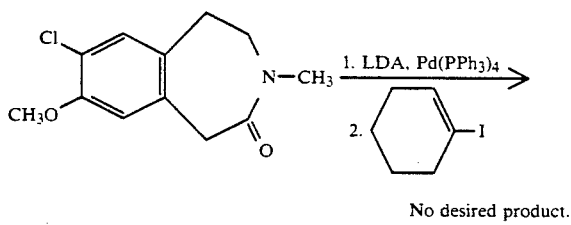

No desired product.

A mixture of 0.75 g. (3.13 mmol.) of 7-chloro-8-methoxy-3-methyl-1,3,4,5-tetrahydro-2H-3-benzazepin-2-one, 0.3 g. (0.26 mmol.) of tetrakis(triphenylphosphine)palladium and 20 ml. of THF was cooled in a dry ice/2-propanol bath to about to −78° C. Under a nitrogen atmosphere 2.1 ml. of 1.5M lithium disopropylamide in cyclohexane (3.13 mmol.) was added through a syringe with stirring. The mixture was kept at −78° C. for an hour. A solution of 0.65 g. (3.13 mmol.) of 1-iodocyclohexene in 10 ml. of THF was then added. The mixture was allowed to warm to room temperature and stirred for an hour, and then heated for 24 hours at 50° C.

The reaction was quenched with 10 ml. of water and then worked up as above. A complicated mixture was obtained. TLC indicated that most of the starting materials remained. The mixture was separated by liquid chromatography (hexane:ethyl acetate 1:1 to 1:4); no desired product was detected by NMR.

EXAMPLE 2

Preparation of further arylacetamides

The following compounds were prepared by the process of Example 1 Part A:

1. (R,S)-7-Chloro-8-methoxy-3-methyl-1-(2-methyl-1-cyclopentenyl)-1,3,4,5-tetrahydro-2H-3-benzazepin-2-one (from 7-chloro-8-methoxy-3-methyl-1,3,4,5-tetrahydro-2H-3-benzazepin-2-one and 2-methyl-1-cyclopentenyl-triflate

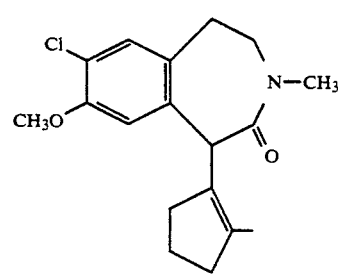

Yield 55%; m.p. 120°–122° C.; TLC (ethyl acetate): $R_f$0.67.

$^1$NMR (300 MHz, CDCl$_3$): δ 1.46 (3H, s), 1.60–1.83 (2H, m), $^1$H 2.15–2.43 (4H, m), 2.94–3.16 (2H, m), 3.07 (3H, s), 3.17–3.30 (1H, m), 3.87 (3H, s) 4.10–4.25 (1H, m), 4.54 (1H, s), 6.69 (1H, s), 7.14 (1H, s).

MS FAB-NBA-DMSO/CH$_2$Cl$_2$, m/e (%): 322 (70), 320 (MH$^+$, 100), 292 (46), 290 (47), 247 (35), 239 (54), 210 (55), 181 (51), 165 (44), 154 (51).

2. (R,S)-7-Chloro-8-methoxy-3-methyl-1-(1,2-dimethyl-1-propenyl)-1,3,4,5-tetrahydro-2H-3-benzazepin-2-one (from 7-chloro-8-methoxy-3-methyl-1,3,4,5-tetrahydro-2H-3-benzazepin-2-one and 1,2-dimethyl-1-propenyl-triflate

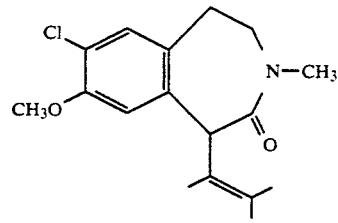

Yield 35%; m.p. 125°–126.5° C.; TLC (ethyl acetate): $R_f$0.65.

$^1$H NMR (300 MHz, CDCl$_3$): δ1.64 (3H,s), 1.78 (6H, bs), 2.93–3.17 (2H, m), 3.07 (3H, s), 3.42–3.54 (1H, m), 3.80–3.98 (1H, m), 3.89 (3H, s), 4.98 (1H, s), 6.71 (1H, s), 7.15 (1H, s).

MS FAB-G/TG - DMSO, m/e (%), 308 (MH$^+$, 100),292 (30), 239 (39), 212 (65), 210 (87).

3. (R,S)-α-(1-cyclohexenyl)-N,N-dimethyl-benzeneacetamide (from N,N-dimethyl-benzeneacetamide and 1-cyclohexenyltriflate

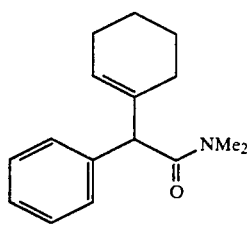

Yield 58%; m.p. 69.5°-71.5° C.; TLC (ethyl acetate): Rf 0.73.

$^1$H NMR (300 MHz, CDCl$_3$): δ 1.83-2.01 (1H, m), 2.12-2.28 (1H, m), 2.29-2.45 (1H, m), 2.46-2.61 (1H, m), 3.05 (3H, s), 3.31-3.52 (2H, m), 4.32 (1H, t,j=7Hz).

MS m/e (%) CI/CH$_4$: 246 (MH+, 100), 113 (53).

4. (R,S)-7-Chloro-8-methoxy-3-methyl-1-phenyl-1,3,4,5-tetrahydro-2H-3-benzazepin-2-one (from 7-chloro-8-methoxy-3-methyl-1,3,4,5-tetrahydro-2H-3-benzazepin-2-one and phenyltriflate)

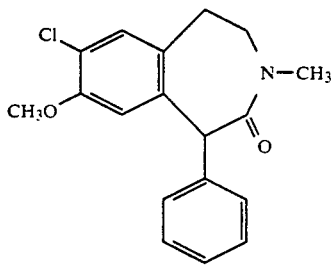

Yield 41%; m.p. 197°-198° C.; TLC (ethyl acetate): Rf 0.60.

$^1$H NMR (300 MHz, CDCl$_3$): δ 2.80-3.15 (3H, m), 3.02 (3H, s), 3.60-3.74 (1H, m), 3.86 (3H, s), 5.25 (1H, s), 6.68 (1H, s), 7.22 (1H, s), 7.02-7.35 (5H, m).

MS Cl+CH$_4$, m/e (%): 316 (MH+, 100), 318 (36).

5. (R,S)-1-(1-Cyclohexenyl)-8-methoxy-3,7-dimethyl-1,3,4,5-tetrahydro-2H-3-benzazepin-2-one (from 8-methoxy-3,7-dimethyl-1,3,4,5-tetrahydro-2H-3-benzazepin-2-one and 1-cyclohexenyl-triflate)

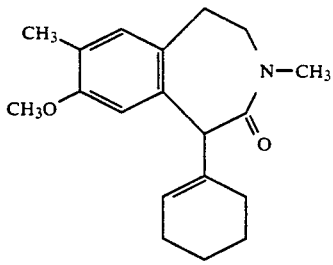

Yield 88%; amorphous solid (no m.p.); TLC (ethyl acetate): Rf 0.67.

$^1$H NMR (300 MHz, CDCl$_3$): δ 1.50-1.75 (4H, m), 1.93-2.20 (4H, m), 2.19 (3H, s), 2.83-3.10 (3H, m), 3.05 (3H, s), 3.77 (3H, s), 4.30-4.42 (2H, m), 5.02 (1H, s), 6.46 (1H, s), 6.88 (1H, s).

MS FAB-NBA-DMSO, m/e (%): 300 (MH+, 100), 299 (77), 298 (48), 272 (13), 270 (20), 241 (18), 227 (15), 219 (20), 190 (29).

EXAMPLE 3

Preparation of 2,3,4,5-Tetrahydro-1H-3-benzazepines

Step A: Preparation of (R)-7-Chloro-8-methoxy-3-methyl-1-(2-methyl-1-cyclopentenyl)-2,3,4,5-tetrahydro-1H-3-benzazepine

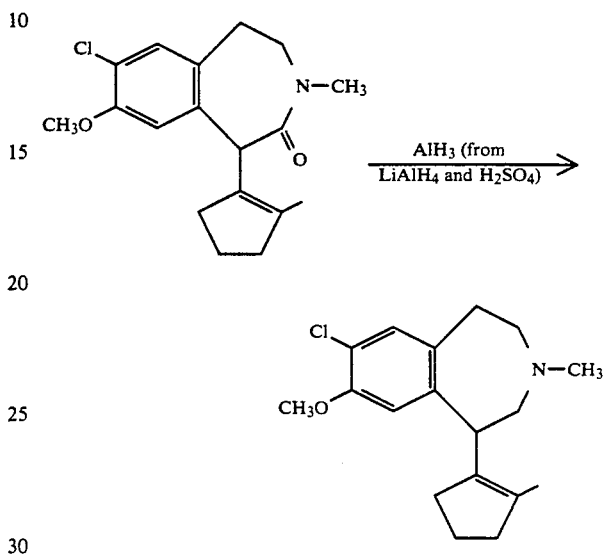

Under a nitrogen atmosphere and cooling in an icebath, a solution of 0.2 g of H$_2$SO$_4$ (2 mmol) in 10 ml of THF was added to a mixture of 0.23 g of LiAlH$_4$ (6 mmol) and 10 ml of THF. This mixture was allowed to warm to room temperature and kept for an hour. With cooling in an ice-bath, a solution of 1.0 g of the lactam (R)-7-chloro-8-methoxy-3-methyl-1-(2-methyl-1-cyclopentenyl)-1,3,4,5-tetrahydro-2H-3-benzazepin-2-one (3 mmol) in 10 ml of THF was added through a syringe. The resulting mixture was stirred for 0.5 hour at room temperature.

A mixture of 20 ml of water and 100 ml of THF was added to quench the reaction, and then 10 ml of 5% NaOH was added to precipitate Al(OH)$_3$. This was filtered off, and the filtrate was concentrated on a rotary evaporator. The residue was dissolved in EtOAc and washed twice with water. The organic layer was dried over Na$_2$SO$_4$.

The crude product obtained by distilling off the solvent and drying under vacuum was recrystallized from EtOAc; yield 0.80 g (84%), m.p. 90°-91° C.

$^1$H NMR (300 MHz, CDCl$_3$): δ 1.60(3H, s), 1.75-2.05 (2H, m), 2.10-2.50 (6H, M), 2.40 (3H, s), 2.66-3.24 (4H, m), 3.80 (3H, s), 4.00-4.10 (1H,d), 6.62 (1H, s), 7.11 (1H, s).

MS FAB-NBA-DMSO, m/e (%): 306 (MH+, 100), 212 (21), 210 (44.5), 197 (23).

Anal.: Calcd. for C$_{18}$H$_{24}$ClNO: C 70.69, H 7.91, N 4.58, Cl 11.59; Found: C 70.89, H 7.86, N 4.70, Cl 11.59.

Step B: Preparation of (R)-7-Chloro-8-hydroxy-3-methyl-1-(2-methyl-1-cyclopentenyl)-2,3,4,5-tetrahydro-1H-3-benzazepine

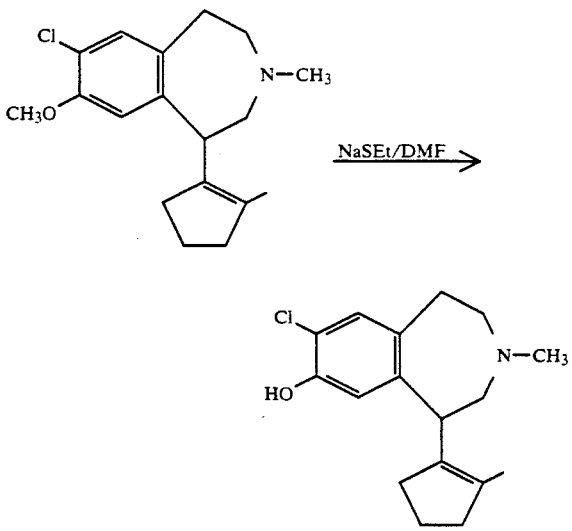

A mixture of 0.310 g of (R)-7-chloro-8-methoxy-3-methyl-1-(2-methyl-1-cyclopentenyl)-2,3,4,5-tetrahydro-1H-3-benzazepine (10 mmol), 6 g of NaSEt (67 mmol) and 50 ml of DMF was heated 140° C. for 6 hours, and then cooled to room temperature. Some acetic acid was added to pH 7-8, and then 25 ml of EtOH and 25 ml of saturated NaHCO$_3$ solution were added. This mixture was heated under house vacuum (a few cm Hg) at 80° C. to remove volatile mercaptan and solvent. The residue was dissolved in EtOAc and the solution was washed with water twice; the organic layer was dried over Na$_2$SO$_4$.

This solution was concentrated on a rotary evaporator, and the residue was recrystallized from EtOAc to yield an off-white solid, 2.14 g (72%), m.p. 186–187 (dec.). It was further recrystallized from EtOAc, m.p. 189–190 (dec.).

$^1$H NMR (300 MHz, CDCl$_3$): δ 1.60 (3H, s), 1.82–2.00 (2H, m), 2.20–2.55 (6H, m), 2.55 (3H, s), 2.70–3.32 (4H, m), 4.05–4.18 (1H, d), 6.68 (1H, s), 7.10 (1H, s).

MS m/e (%) Cl+/CH$_4$: 292 (MH+, 100), 258 (19); (EI) 291 (M, 19%), 219 (8), 183 (13), 136 (18).

Anal.: Calcd. for C$_{17}$H$_{22}$ClNO: C 69.97, H 7.60, N 4.80, Cl 12.15; found: C 69.94, H 7.47, N 4.85, Cl 11.89.

High resolution MS: Calcd for C$_{17}$H$_{23}$ClNO+ (MH+): 292.1468; found: 292.1461.

This free base was dissolved in EtOAc, and a solution of HCl in Et$_2$O was added to pH~3 to precipitate the white HCl salt, which was filtered off and washed twice with ether; yield (dry): 1.97 g, m.p. 263° C. (dec.).

$^1$H NMR (300 MHz, DMSO): δ 1.15 (3H, s), 1.8-2.1 (2H, m), 2.22–2.55 (4H, m), 2.80 (3H, s), 2.7–3.25 (4H, m), 3.25–3.7 (4H, m), 4.35–4.62 (1H, d), 6.70 (1H, s), 7.22 (1H, s).

Anal.: Calcd. for C$_{17}$H$_{23}$Cl$_2$NO: C 62.20, H 7.06, N 4.27, Cl 21.60; found: C 62.32, H 7.00, N 4.33, Cl 21.16.

The following compounds can also be prepared by the novel process of the present invention, especially by the processes exemplified in the foregoing Examples:

1,3,4,5-Tetrahydro-2H-3-benzazepin-2-ones:
(R,S)-7-chloro-1-(1-cyclohexenyl)-8-methoxy-3-methyl-1,3,4,5-tetrahydro-2H-3-benzazepin-2-one and its (R)- and (S)- isomers;
(R,S)-1-(1-cyclohexenyl)-8-methoxy-3,7-dimethyl-1,3,4,5-tetrahydro-2H-3-benzazepin-2-one and its (R)- and (S)- isomers;
(R,S)-7-chloro-1-(1-cyclopentenyl)-8-methoxy-3-methyl-1,3,4,5-tetrahydro-2H-3-benzazepin-2-one and its (R)- and (S)- isomers;
(R,S)-7-chloro-8-methoxy-3-methyl-(2-methyl-1-cyclopentenyl)-1,3,4,5-tetrahydro-2H-3-benzazepin-2-one and its (R)- and (S)- isomers;
(R,S)-7-chloro-8-methoxy-3-methyl-1-(2-methyl-1-cyclohexenyl)-1,3,4,5-tetrahydro-2H-3-benzazepin-2-one and its (R)- and (S)- isomers; and
(R,S)-7-chloro-8-methoxy-3-methyl-1-(1,2-dimethyl-1-propenyl)-1,3,4,5-tetrahydro-2H-3-benzazepin-2-one and its (R)- and (S)- isomers.

2,3,4,5-Tetrahydro-1H-3-benzazepines (by reduction and demethylation of the compounds listed above):
(R,S)-7-chloro-1-(1-cyclohexenyl)-8-hydroxy-3-methyl-2,3,4,5-tetrahydro-1H-3-benzazepine, m.p. of hydrobromide 177°–179° C.;
(R,S)-1-(1-cyclohexenyl)-8-hydroxy-3,7-dimethyl-2,3,4,5-tetrahydro-1H-3-benzazepine (as hydrochloride);
(R,S)-7-chloro-1-(1-cyclopentenyl)-8-hydroxy-3-methyl-2,3,4,5-tetrahydro-1H-3-benzazepine, m.p. of free base 186°–188° C.;
(R,S)-7-chloro-8-hydroxy-3-methyl-(2-methyl-1-cyclopentenyl)-2,3,4,5-tetrahydro-1H-3-benzazepine (as hydrochloride); and
(R,S)-7-chloro-8-hydroxy-3-methyl-1-(2-methyl-1-cyclohexenyl)-2,3,4,5-tetrahydro-1H-3-benzazepine (as hydrochloride).

Resolved enantiomers of 2,3,4,5-tetrahydro-1H-3-benzazepines:
(R)-1-(1-cyclohexenyl)-8-hydroxy-3,7-dimethyl-2,3,4,5-tetrahydro-1H-3-benzazepine (as hydrochloride);
(S)-1-(1-cyclohexenyl)-8-hydroxy-3,7-dimethyl-2,3,4,5-tetrahydro-1H-3-benzazepine (as hydrochloride);
(R)-7-chloro-1-(1-cyclohexenyl)-8-hydroxy-3-methyl-2,3,4,5-tetrahydro-1H-3-benzazepine (as hydrochloride);
(S)-7-chloro-1-(1-cyclohexenyl)-8-hydroxy-3-methyl-2,3,4,5-tetrahydro-1H-3-benzazepine (as hydrochloride);
(R)-7-chloro-8-hydroxy-3-methyl-(2-methyl-1-cyclopentenyl)-2,3,4,5-tetrahydro-1H-3-benzazepine, m.p. of hydrochloride 249°–251°C. (dec.);
(S)-7-chloro-8-hydroxy-3-methyl-1-(1,2-dimethyl-1-propenyl)2,3,4,5-tetrahydro-1H-3-benzazepine (as hydrochloride);
(R)-7-chloro-8-hydroxy-3-methyl-(2-methyl-1-cyclopentenyl)-2,3,4,5-tetrahydro-1H-3-benzazepine, m.p. of hydrochloride 248°–249° C. (dec.); and
(S)-7-chloro-8-hydroxy-3-methyl-(2-methyl-1-cyclopentenyl)-2,3,4,5-tetrahydro-1-H-3-benzazepine, m.p. of hydrochloride 248°–249° C. (dec.).

Also:
(R)-7-chloro-8-hydroxy-3-methyl-1-phenyl 2,3,4,5-tetrahydro-1-H-3-benzazepine (SCH 23390).

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to explain the principles of the invention clearly and thereby enable others skilled in the art to utilize the

We claim:
1. A compound of the formula

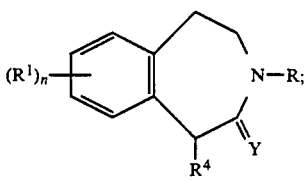

(II)

wherein
n is 0, 1, 2, 3 or 4;
each $R^1$ is independently selected from alkenyl, alkoxy, hydroxy, alkenyloxy, cycloalkyl, nitro, halogen, phenyl and phenoxy, or two groups $R^1$ in adjacent positions optionally form an alkylenedioxy group or a fused benzene ring, and the phenyl or phenoxy group or the fused benzene ring is optionally substituted by a group selected form alkyl, alkenyl, alkoxy, hydroxy, alkenyloxy, cycloalkyl, nitro, halogen, and alkylenedioxy;
$R^4$ is a 1-cycloalkenyl group;
R is an alkyl, alkenyl, aryl, aralkyl, cycloalkyl or cycloalkylalkyl group;
and Y is an oxygen atom or $H_2$;
and its non-toxic salts with bases when $R^1$ is or contains a hydroxy group;
and its non-toxic acid addition salts; wherein
alkenyl, including the alkenyl portion of alkenyloxy, represents a straight or branched hydrocarbon chain having at least one carbon-to-carbon double bond and having from 2 to 10 carbon atoms:
alkyl, including the alkyl portion of alkoxy, cycloalkylalkyl and aralkyl, represents a straight or branched, saturated hydrocarbon chain having from 1 to 10 carbon atoms;
alkylene (in alkylenedioxy) represents a straight or branched, saturated hydrocarbon chain having from 1 to 6 carbon atoms:
aryl, including the aryl portion of aralkyl groups, represents phenyl, substituted phenyl, 1-naphythyl, 2-naphthyl and indanyl:
cycloalkenyl represents a carbocyclic group having from 5 to 8 carbon atoms and one, two or three carbon-to-carbon double bonds in the ring, and optionally bearing one or two lower alkyl substituents:
lower alkyl represents a straight or branched, saturated hydrocarbon chain having from 1 to 6 carbon atoms:
cycloalkyl, including the cycloalkyl portion of cycloalkylalkyl, represents a saturated carbocyclic ring having from 3 to 8 carbon atoms;
substituted phenyl represents a phenyl group in which 1 to 3 hydrogen atoms thereof are replaced by the same or different substituents independently chosen from alkyl, alkenyl, alkoxy, alkenyloxy, nitro, halogen, trifluoromethyl, cyano, cycloalkyl, and alkynyloxy, or wherein two hydrogen atoms in adjacent positions are replaced by alkylenedioxy.

2. A compound of the formula II defined in claim 1 wherein:
n is 1 or 2;
each $R^1$ is independently selected from lower alkoxy, hydroxy, halogen, nitro or phenoxy;
$R^4$ is a 1-cycloalkenyl group;
R is a lower alkyl group;
and Y is $H_2$;
and its non-toxic salts with bases when $R^1$ is or contains a hydroxy group;
and its non-toxic acid addition salts;
wherein lower alkyl, including the alkyl portion of lower alkoxy, represents a straight or branched, saturated hydrocarbon chain having from 1 to 6 carbon atoms.

3. A compound as claimed in claim 1 having the formula

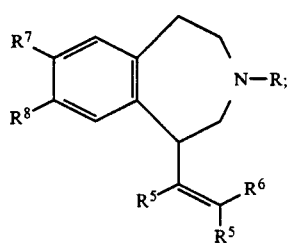

(IIA)

wherein R is as defined in claim 11;
the two groups $R^5$ together form a pentamethylene, a trimethylene or a tetramethylene group;
$R^6$ is a lower alkyl group or a hydrogen atom;
and each of $R^7$ and $R^8$ is independently selected from lower alkoxy, hydroxy and halogen;
and its non-toxic salts with bases;
and its non-toxic acid addition salts;
wherein lower alkyl, including the alkyl portion of lower alkoxy, represents a straight or branched, saturated hydrocarbon chain having from 1 to 6 carbon atoms.

4. A compound and its salts as claimed in claim 3 wherein
R is a methyl group;
the two groups $R^5$ together form a trimethylene or a tetramethylene group;
$R^7$ is halogen and $R^8$ is hydroxy.

5. A compound and its salts as claimed in claim 4 wherein $R^7$ is methyl or chlorine.

6. A compound as claimed in claim 1, namely one selected from the group consisting of:
(R,S)-7-chloro-1-(1-cyclohexenyl)-8-methoxy-3-methyl-1,3,4,5-tetrahydro-2H-3-benzazepin-2-one and its (R)- and (S)- isomers;
(R,S)-1-(1-cyclohexenyl)-8-methoxy-3,7-dimethyl-1,3,4,5-tetrahydro-2H-3-benzazepin-2-one and its (R)- and (S)- isomers;
(R,S)-7-chloro-1-(1-cyclopentenyl)-8-methoxy-3-methyl-1,3,4,5-tetrahydro-2H-3-benzazepin-2-one and its (R)- and (S)- isomers;
(R,S)-7-chloro-8-methoxy-3-methyl-1-(2-methyl-1-cyclopentenyl)-1,3,4,5-tetrahydro-2H-3-benzazepin-2-one and its (R)- and (S)- isomers;
(R,S)-7-chloro-8-methoxy-3-methyl-1-(2-methyl-1-cyclohexenyl)-1,3,4,5-tetrahydro-2H-3-benzazepin-2-one and its (R)- and (S)- isomers; and (R,S)-7-chloro-8-methoxy-3-methyl-1-(1,2-dimethyl-1-propenyl)-1,3,4,5-tetrahydro-2H-3-benzazepin-2-one and its (R)- and (S)- isomers.

7. A compound as claimed in claim 3, namely one selected from the group consisting of:
(R,S)-7-chloro-1-(1-cyclohexenyl)-8-hydroxy-3-methyl-2,3,4,5-tetrahydro-1H-3-benzazepine;
(R,S)-1-(1-cyclohexenyl)-8-hydroxy-3,7-dimethyl-2,3,4,5-tetrahydro-1H-3-benzazepine;
(R,S)-7-chloro-1-(1-cyclopentenyl)-8-hydroxy-3-methyl-2,3,4,5-tetrahydro-1H-3-benzazepine;
(R,S)-7-chloro-8-hydroxy-3-methyl-1-(2-methyl-1-cyclopentenyl)-2,3,4,5-tetrahydro-1H-3-benzazepine; and
(R,S)-7-chloro-8-hydroxy-3-methyl-1-(2-methyl-1-cyclohexenyl)-2,3,4,5-tetrahydro-1H-3-benzazepine.

8. A compound as claimed in claim 3, namely one selected from the group consisting of:
(R)-1-(1-Cyclohexenyl)-8-hydroxy-3,7-dimethyl-2,3,4,5-tetrahydro-1H-3-benzazepine;
(S)-1-(1-cyclohexenyl)-8-hydroxy-3,7-dimethyl-2,3,4,5-tetrahydro-1H-3-benzazepine;
(R)-7-chloro-1-(1-cyclohexenyl)-8-hydroxy-3-methyl-2,3,4,5-tetrahydro-1H-3-benzazepine;
(S)-7-chloro-1-(1-cyclohexenyl)-8-hydroxy-3-methyl-2,3,4,5-tetrahydro-1H-3-benzazepine;
(S)-7-chloro-8-hydroxy-3-methyl-1-(1,2-dimethyl-1-propenyl)-2,3,4,5-tetrahydro-1H-3-benzazepine;
(R)-7-chloro-8-hydroxy-3-methyl-1-(2-methyl-1-cyclopentenyl)-2,3,4,5-tetrahydro-1H-3-benzazepine; and
(S)-7-chloro-8-hydroxy-3-methyl-1-(2-methyl-1-cyclopentenyl)-2,3,4,5-tetrahydro-1H-3-benzazepine.

9. A compound as claimed in claim 3. namely:
(R)-7-Chloro-8-hydroxy-3-methyl-1-(2-methyl-1-cyclopentenyl)-2,3,4,5-tetrahydro-1H-3-benzazepine.

10. A salt as claimed in claim 1 formed with hydrochloric, sulfuric, phosphoric, acetic, citric, oxaclic, malonic, salicyclic, malic, fumaric, succinic, ascorbic, maleic, or methanesulfonic acid.

11. A salt as claimed in claim 1 in the form of its sodium, potassium or calcium salt.

* * * * *

UNITED STATES PATENT AND TRADEMARK OFFICE
CERTIFICATE OF CORRECTION

PATENT NO. : 5,241,065
DATED : Aug. 31, 1993
INVENTOR(S) : Joel G. Berger, Wei K. Chang, Joseph A. Kozlowski, Guowei Zhou.

It is certified that error appears in the above-identified patent and that said Letters Patent is hereby corrected as shown below:

| | |
|---|---|
| Column 2 line 62: | Delete "estercarbonyl" and insert --ester-carbonyl-- |
| Column 2 line 63: | Delete "trite" and insert --trile-- |
| Column 3 line 33: | Delete "N" and insert --n-- |
| Column 23 line 26: | Delete "form" and insert --from-- |
| Column 23 line 49: | Delete "naphythyl" and insert --naphthyl-- |
| Column 24 line 31: | Delete "11" and insert --1-- |
| Column 26 line 18: | Delete "oxaclic" and insert --oxalic-- |
| Column 26 line 19: | Delete "salicyclic" and insert --salicylic-- |

Signed and Sealed this

Twenty-second Day of March, 1994

Attest:

BRUCE LEHMAN

*Attesting Officer*  *Commissioner of Patents and Trademarks*